(12) United States Patent
Pomytkin et al.

(10) Patent No.: US 8,298,523 B2
(45) Date of Patent: Oct. 30, 2012

(54) COMPOSITIONS CONTAINING INTERLEUKIN-1 AND PEPTIDES

(75) Inventors: Igor Anatolievich Pomytkin, Moscow (RU); Igor Arturovic Petropavlov, Küsnacht (CH)

(73) Assignee: United Technologies UT AG, Zurich (CH)

( * ) Notice: Subject to any disclaimer, the term of this patent is extended or adjusted under 35 U.S.C. 154(b) by 0 days.

(21) Appl. No.: 13/124,272

(22) PCT Filed: Nov. 7, 2008

(86) PCT No.: PCT/EP2008/065152
§ 371 (c)(1), (2), (4) Date: Apr. 14, 2011

(87) PCT Pub. No.: WO2010/051852
PCT Pub. Date: May 14, 2010

(65) Prior Publication Data
US 2011/0189126 A1    Aug. 4, 2011

(51) Int. Cl.
A61K 38/20 (2006.01)
A61K 7/40 (2006.01)
A61K 7/48 (2006.01)

(52) U.S. Cl. ........ 424/85.2; 514/1.1; 514/18.6; 514/18.8

(58) Field of Classification Search .................. None
See application file for complete search history.

(56) References Cited

U.S. PATENT DOCUMENTS

| | | |
|---|---|---|
| 4,816,436 A | 3/1989 | Jacobs |
| 5,035,887 A | 7/1991 | Antoniades et al. |
| 5,120,534 A | 6/1992 | Hirai et al. |
| 5,202,118 A | 4/1993 | Gillis et al. |
| 5,534,251 A | 7/1996 | Sugahara et al. |

FOREIGN PATENT DOCUMENTS

| | | |
|---|---|---|
| EP | 0391444 | 10/1990 |
| EP | 0482213 | 4/1992 |
| EP | 1892247 | 2/2008 |
| ES | 2121782 | 4/1992 |
| JP | 4018033 | 1/1992 |
| RU | 2017488 | 8/1994 |
| RU | 2230549 | 6/2004 |
| RU | 2286140 | 10/2006 |
| WO | WO8905653 | 6/1989 |
| WO | WO 91/16916 | 11/1991 |
| WO | WO9736922 | 10/1997 |
| WO | WO2009129857 | * 10/2009 |

OTHER PUBLICATIONS

Wang Zhaohui; et al, "The interaction of interleukin-1 and opioid peptides in cultured rat corticocerebral cells", Chemical Abstracts Service, Nov. 30, 1995, XP 002530286.
Vinogradov V A; et al, "Opioid Activity of Peptides and Skin Wound Healing", Biosciences Information Service, 1987, XP 002509588.
Kipper S. N., "Cream for sensitive skin", Chemical Abstracts Service, Oct. 27, 2006, XP002530287.
Zavyalov, A.V., "Dalargin for psoriasis treatment", Chemical Abstracts Service, Nov. 21, 1995, XP002530288.
Tereshin, K. Ya. et al, "Methods for treatment of allergic dematosis", Chemical Abstracts Service, Aug. 11, 2004, XP002530289.
Charles A. Dinarello, The interleukin-1 family: 10 years of discovery, The FASEB Journal, vol. B. Dec. 1994, pp. 1314-1325.
Simon W. Lee et al., Autocrine Stimulation of Interleukin-1α and Transforming . . . , Journal of Investigative Dermatology, 97: 106-110, 1991.

* cited by examiner

*Primary Examiner* — Prema Mertz
(74) *Attorney, Agent, or Firm* — Notaro, Michalos & Zaccaria P.C.

(57) ABSTRACT

The present invention relates to pharmaceutical, dermatological, cosmeceutical, or cosmetic compositions comprising (a) interleukin-1 family members consisting of interleukin-1 alpha, interleukin-1 family member 5 (delta), interleukin-1 family member 6 (epsilon), interleukin-1 family member 7 (zeta), interleukin-1 family member 8 (eta), interleukin-1 family member 9, interleukin-1 family member 10 (theta), and interleukin-18; (b) a peptide of the general formula (I): Tyr-$X_1$-$X_2$-Phle-$X_3$-$X_4$-Y, wherein $X_1$ is Gly, L-Ala or D-Ala; $X_2$ is Gly, L-Ala or D-Ala; $X_3$ is absent or independently Leu, Met, Iie, or Val; $X_4$ is absent or independently Ala, Asp, Asn, Glu, Gln, Pro, Arg, Gly, Lys, Thr, or Ser; Y is absent or a sequence of 1 to 5 amino acid residues; and acceptable carriers or diluents.

16 Claims, No Drawings

COMPOSITIONS CONTAINING INTERLEUKIN-1 AND PEPTIDES

FIELD OF THE INVENTION

The present invention relates to pharmaceutical, dermatological, cosmeceutical, and cosmetic compositions comprising interleukin-1 family members and peptide of general formula Tyr-$X_1$-$X_2$-Phe-$X_3$-$X_4$-Y.

BACKGROUND OF THE INVENTION

Interleukin-1 family consists of interleukin-1 alpha, beta, delta, epsilon, zeta, eta, theta, which are also named IL-1F1, IL1F2, IL1F3, IL1F4, IL1F5, IL1F6, IL1F7, IL1F8, IL1F9, and interleukin-18. These are naturally occurring polypeptides with sequences well-known from the art. The first member of this family, interleukin-1 alpha is synthesized as 31-kDa precursor, and is secreted by cells in active form of about 18-kDa. Interleukin-1 alpha is the only interleukin-1 family member that is constitutively produced in active form by cells of mammalian epidermis including human epidermis. Healthy human skin contains interleukin-1 alpha in levels of about 10 to 20 ng/cm², which levels are frequently decreased, for example, in conditions of psoriatic or aging skin. Mizutani H, et al., *J Clin Invest.* 1991, 87(3):1066-71. Wood L C, et al., *J Clin Invest* 1992: 90: 482-487. Se Kyoo Jeonq, et al., *Exp. Dermatology* 2005: 14: 571-579. Chantel O., et al., *J Invest Dermatol* 122:330-336, 2004. Nowinski D, et al, *J Invest Dermatol.* 2002; 119(2):449-55. Bonifati C, et al., *J Biol Requl Homeost Agents.* 1997, 11(4):133-6. Takematsu H, et al. Tohoku *J Exp Med.* 1990, 161(3):159-69.

The use of interleukin-1 family members in medicinal applications is known from the art. For example, U.S. Pat. No. 4,816,436 discloses a process for treating arthritis or inflammation with the use of intra-articular, intramuscular, intravenous, or intraperitoneal injections of interleukin-1 alpha; U.S. Pat. No. 5,120,534 discloses a method for treating thrombocytopenia by administering interleukin-1 alpha or Asp36, Ser141-derivative of interleukin-1 alpha; U.S. Pat. No. 5,534,251 discloses stabilized medicinal composition comprising Asp36, Ser141-derivative of interleukin-1 alpha; EP0391444 discloses a pharmaceutical composition comprising interleukin-1 alpha, and suitable for forming a parenterally administratable aqueous formulation; WO9116916, JP4018033, EP0482213, and ES2121782T disclose an antitumor composition containing the combination of interleukin-1 and gamma-interferon.

However, no published or disclosed in the art related to cosmetic, cosmeceutical, or dermatological compositions comprising interleukin-1 family member and a peptide of the general formula Tyr-$X_1$-$X_2$-Phe-$X_3$-$X_4$-Y, wherein $X_1$, $X_2$, $X_3$, $X_4$ are independently amino acids, and Y is absent or a sequence of 1 to 5 amino acid residues.

The use of interleukin-1 family members in medicinal or cosmetic applications may be limited by side effects linked to pro-inflammatory action of these polypeptides. Thus, there is a great need in agents, which may diminish side effects of interleukin-1 family members.

We found that the use of peptide of general formula Tyr-$X_1$-$X_2$-Phe-$X_3$-$X_4$-Y, wherein $X_1$, $X_2$, $X_3$, $X_4$ are independently amino acids, and Y is absent or a sequence of 1 to 5 amino acid residues, remarkably eliminates undesirable effects of polypeptides of interleukin-1 family members, when said peptides are used in combination with said polypeptides.

It is an object of the present invention to provide pharmaceutical, cosmetic, cosmeceutical, and dermatological compositions comprising interleukin-1 family members and peptide of general formula Tyr-$X_1$-$X_2$-Phe-$X_3$-$X_4$-Y.

DETAILED DESCRIPTION OF THE INVENTION

The present invention provides a composition comprising: (a) a polypeptide selected from the group of interleukin-1 family members consisting of interleukin-1 alpha, interleukin-1 family member 5 (delta), interleukin-1 family member 6 (epsilon), interleukin-1 family member 7 (zeta), interleukin-1 family member 8 (eta), interleukin-1 family member 9, interleukin-1 family member 10 (theta), and interleukin-18; and (b) a peptide of the general formula (I):

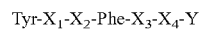

Tyr-$X_1$-$X_2$-Phe-$X_3$-$X_4$-Y wherein
$X_1$ is Gly, L-Ala or D-Ala;
$X_2$ is Gly, L-Ala or D-Ala;
$X_3$ is absent or independently Leu, Met, Ile, or Val;
$X_4$ is absent or independently Ala, Asp, Asn, Glu, Gln, Pro, Arg, Gly, Lys, Thr, or Ser;
Y is absent or a sequence of 1 to 5 amino acid residues.

Further, the present invention provides a pharmaceutical composition comprising: (a) a polypeptide selected from the group of interleukin-1 family members consisting of interleukin-1 alpha, interleukin-1 family member 5 (delta), interleukin-1 family member 6 (epsilon), interleukin-1 family member 7 (zeta), interleukin-1 family member 8 (eta), interleukin-1 family member 9, interleukin-1 family member 10 (theta), and interleukin-18; and (b) a peptide of the general formula (I):

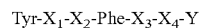

Tyr-$X_1$-$X_2$-Phe-$X_3$-$X_4$-Y wherein
$X_1$ is Gly, L-Ala or D-Ala;
$X_2$ is Gly, L-Ala or D-Ala;
$X_3$ is absent or independently Leu, Met, Ile, or Val;
$X_4$ is absent or independently Ala, Asp, Asn, Glu, Gln, Pro, Arg, Gly, Lys, Thr, or Ser;
Y is absent or a sequence of 1 to 5 amino acid residues; and
(c) a pharmaceutically acceptable diluent or carrier.

Further, the present invention provides dermatological composition comprising:
(a) a polypeptide selected from the group of interleukin-1 family members consisting of interleukin-1 alpha, interleukin-1 family member 5 (delta), interleukin-1 family member 6 (epsilon), interleukin-1 family member 7 (zeta), interleukin-1 family member 8 (eta), interleukin-1 family member 9, interleukin-1 family member 10 (theta), and interleukin-18;
(b) a peptide of the general formula (I):

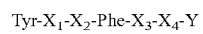

Tyr-$X_1$-$X_2$-Phe-$X_3$-$X_4$-Y wherein
$X_1$ is Gly, L-Ala or D-Ala;
$X_2$ is Gly, L-Ala or D-Ala;
$X_3$ is absent or independently Leu, Met, Ile, or Val;
$X_4$ is absent or independently Ala, Asp, Asn, Glu, Gln, Pro, Arg, Gly, Lys, Thr, or Ser;
Y is absent or a sequence of 1 to 5 amino acid residues; and
(c) a dermatologically acceptable diluent or carrier.

Further, the present invention provides cosmetic or cosmeceutical composition comprising:
(a) a polypeptide selected from the group of interleukin-1 family members consisting of interleukin-1 alpha, interleukin-1 family member 5 (delta), interleukin-1 family member 6 (epsilon), interleukin-1 family member 7 (zeta), interleukin-1 family member 8 (eta), interleukin-1 family member 9, interleukin-1 family member 10 (theta), and interleukin-18;

(b) a peptide of the general formula (I):

Tyr-$X_1$-$X_2$-Phe-$X_3$-$X_4$-Y wherein $X_1$ is Gly, L-Ala or D-Ala;

$X_2$ is Gly, L-Ala or D-Ala;

$X_3$ is absent or independently Leu, Met, Ile, or Val;

$X_4$ is absent or independently Ala, Asp, Asn, Glu, Gln, Pro, Arg, Gly, Lys, Thr, or Ser;

Y is absent or a sequence of 1 to 5 amino acid residues; and (c) a dermatologically acceptable diluent or carrier.

Preferably, the polypeptide of the present invention is interleukin-1 alpha. In preferred embodiments of the present invention, the content of interleukin-1 alpha in said compositions is in the range from $10^{-7}$ to $10^{-4}$ wt. %.

In preferred embodiments of the present invention, said compositions further comprise a buffer at a concentration effective to maintain the pH of the composition at between about 4.0 to about 7.5. Examples of such buffers include, but are not limited to, phosphate buffer, acetate, citrate buffer, succinate buffer, and glycine buffer.

As used herein, the term "interleukin-1 alpha" refers to a protein having the following amino acid sequence and structure (naturally occurring human interleukin-1 alpha), and biologically active analogues and derivatives thereof:

Ser-Ala-Pro-Phe-Ser-Phe-Leu-Ser-Asn-Val-Lys-Tyr-
Asn-Phe-Met-Arg-Ile-Ile-Lys-Tyr-Glu-Phe-Ile-Leu-
Asn-Asp-Ala-Leu-Asn-Gln-Ser-Ile-Ile-Arg-Ala-Asn-
Asp-Gln-Tyr-Leu-Thr-Ala-Ala-Ala-Leu-His-Asn-Leu-
Asp-Glu-Ala-Val-Lys-Phe-Asp-Met-Gly-Ala-Tyr-Lys-
Ser-Ser-Lys-Asp-Asp-Ala-Lys-Ile-Thr-Val-Ile-Leu-
Arg-Ile-Ser-Lys-Thr-Gln-Leu-Tyr-Val-Thr-Ala-Gln-
Asp-Glu-Asp-Gln-Pro-Val-Leu-Leu-Lys-Glu-Met-Pro-
Glu-Ile-Pro-Lys-Thr-Ile-Thr-Gly-Ser-Glu-Thr-Asn-
Leu-Leu-Phe-Phe-Trp-Glu-Thr-His-Gly-Thr-Lys-Asn-
Tyr-Phe-Thr-Ser-Val-Ala-His-Pro-Asn-Leu-Phe-Ile-
Ala-Thr-Lys-Gln-Asp-Tyr-Trp-Val-Cys-Leu-Ala-Gly-
Gly-Pro-Pro-Ser-Ile-Thr-Asp-Phe-Gln-Ile-Leu-Glu-
Asn-Gln-Ala

The term thus includes interleukin-1 alpha which is chemically synthesized or expressed using recombinant protein expression systems that use, for example, E-coli or yeast as the host. A preferred interleukin-1 alpha is human interleukin-1 alpha expressed using a protein expression system.

As used herein, the term "analogue of interleukin-1 alpha" refers to an interleukin-1 alpha that contains one or more amino acid substitutions, deletions, additions, or rearrangements compared with human interleukin-1 alpha at sites such that the interleukin-1 alpha analogue still retains the in vivo biological activity of interleukin-1 alpha. Examples of interleukin-1 alpha analogues include Asp36-interleukin-1 alpha and Ser141-interleukin-1 alpha.

Interleukin-1 alpha derivatives include naturally occurring interleukin-1 alpha and interleukin-1 alpha analogues that are chemically or enzymatically derivatized at one or more constituent amino acids, including side chain modifications, backbone modifications, and N- and C-terminal modifications, by for example acetylation, acylation, hydroxylation, methylation, amidation, phosphorylation, pegylation, or glycosylation, and that retain the in vivo biological activity of interleukin-1 alpha. An example of an interleukin-1 alpha derivative is N6-myristoyl-Lys11-interleukin-1 alpha and HisTag-interleukin-1 alpha.

As used herein, the term "amino acid" refers to the natural amino acids, e.g. Asp, Asn, Arg, Cys, Glu, Gln, Gly, His, Ile, Leu, Lys, Met, Phe, Ser, Thr, Tyr, and Val. Such amino acids may be in L- or D-form.

In the preferred embodiments of the present invention, the peptide of the general formula (I) contains amino acid residues in L-form.

In some of the preferred embodiments of the present invention, the peptide of the general formula (I) contains alanine residue in D-form.

In the preferred embodiments of the present invention, the peptide of the general formula (I) is selected from the group consisting of:

```
Tyr-Gly-Gly-Phe-Leu-Asp          (SEQ ID NO: 1)
Tyr-L-Ala-Gly-Phe-Leu-Asp        (SEQ ID NO: 2)
Tyr-D-Ala-Gly-Phe-Leu-Asp        (SEQ ID NO: 3)
Tyr-Gly-Gly-Phe-Ile-Asp          (SEQ ID NO: 4)
Tyr-L-Ala-Gly-Phe-Ile-Asp        (SEQ ID NO: 5)
Tyr-D-Ala-Gly-Phe-Ile-Asp        (SEQ ID NO: 6)
Tyr-Gly-Gly-Phe-Met-Asp          (SEQ ID NO: 7)
Tyr-L-Ala-Gly-Phe-Met-Asp        (SEQ ID NO: 8)
Tyr-D-Ala-Gly-Phe-Met-Asp        (SEQ ID NO: 9)
Tyr-Gly-Gly-Phe-Val-Asp          (SEQ ID NO: 10)
Tyr-L-Ala-Gly-Phe-Val-Asp        (SEQ ID NO: 11)
Tyr-D-Ala-Gly-Phe-Val-Asp        (SEQ ID NO: 12)
Tyr-Gly-Gly-Phe-Leu-Asn          (SEQ ID NO: 13)
Tyr-L-Ala-Gly-Phe-Leu-Asn        (SEQ ID NO: 14)
Tyr-D-Ala-Gly-Phe-Leu-Asn        (SEQ ID NO: 15)
Tyr-Gly-Gly-Phe-Ile-Asn          (SEQ ID NO: 16)
Tyr-L-Ala-Gly-Phe-Ile-Asn        (SEQ ID NO: 17)
Tyr-D-Ala-Gly-Phe-Ile-Asn        (SEQ ID NO: 18)
Tyr-Gly-Gly-Phe-Met-Asn          (SEQ ID NO: 19)
Tyr-L-Ala-Gly-Phe-Met-Asn        (SEQ ID NO: 20)
Tyr-D-Ala-Gly-Phe-Met-Asn        (SEQ ID NO: 21)
Tyr-Gly-Gly-Phe-Val-Asn          (SEQ ID NO: 22)
Tyr-L-Ala-Gly-Phe-Val-Asn        (SEQ ID NO: 23)
Tyr-D-Ala-Gly-Phe-Val-Asn        (SEQ ID NO: 24)
Tyr-Gly-Gly-Phe-Leu-Glu          (SEQ ID NO: 25)
```

-continued

| | |
|---|---|
| Tyr-Ala-Gly-Phe-Leu-Glu | (SEQ ID NO: 26) |
| Tyr-D-Ala-Gly-Phe-Leu-Glu | (SEQ ID NO: 27) |
| Tyr-Gly-Gly-Phe-Ile-Glu | (SEQ ID NO: 28) |
| Tyr-L-Ala-Gly-Phe-Ile-Glu | (SEQ ID NO: 29) |
| Tyr-D-Ala-Gly-Phe-Ile-Glu | (SEQ ID NO: 30) |
| Tyr-Gly-Gly-Phe-Met-Glu | (SEQ ID NO: 31) |
| Tyr-L-Ala-Gly-Phe-Met-Glu | (SEQ ID NO: 32) |
| Tyr-D-Ala-Gly-Phe-Met-Glu | (SEQ ID NO: 33) |
| Tyr-Gly-Gly-Phe-Val-Glu | (SEQ ID NO: 34) |
| Tyr-L-Ala-Gly-Phe-Val-Glu | (SEQ ID NO: 35) |
| Tyr-D-Ala-Gly-Phe-Val-Glu | (SEQ ID NO: 36) |
| Tyr-Gly-Gly-Phe-Leu-Gln | (SEQ ID NO: 37) |
| Tyr-Ala-Gly-Phe-Leu-Gln | (SEQ ID NO: 38) |
| Tyr-D-Ala-Gly-Phe-Leu-Gln | (SEQ ID NO: 39) |
| Tyr-Gly-Gly-Phe-Ile-Gln | (SEQ ID NO: 40) |
| Tyr-L-Ala-Gly-Phe-Ile-Gln | (SEQ ID NO: 41) |
| Tyr-D-Ala-Gly-Phe-Ile-Gln | (SEQ ID NO: 42) |
| Tyr-Gly-Gly-Phe-Met-Gln | (SEQ ID NO: 43) |
| Tyr-L-Ala-Gly-Phe-Met-Gln | (SEQ ID NO: 44) |
| Tyr-D-Ala-Gly-Phe-Met-Gln | (SEQ ID NO: 45) |
| Tyr-Gly-Gly-Phe-Val-Gln | (SEQ ID NO: 46) |
| Tyr-L-Ala-Gly-Phe-Val-Gln | (SEQ ID NO: 47) |
| Tyr-D-Ala-Gly-Phe-Val-Gln | (SEQ ID NO: 48) |
| Tyr-D-Ala-Gly-Phe-Leu-Arg | (SEQ ID NO: 49) |
| Tyr-D-Ala-Gly-Phe-Leu-Gly | (SEQ ID NO: 50) |
| Tyr-D-Ala-Gly-Phe-Leu-Lys | (SEQ ID NO: 51) |
| Tyr-D-Ala-Gly-Phe-Leu-Thr | (SEQ ID NO: 52) |
| Tyr-D-Ala-Gly-Phe-Leu-Ser | (SEQ ID NO: 53) |
| Tyr-D-Ala-Gly-Phe-Leu-Pro | (SEQ ID NO: 54) |
| Tyr-D-Ala-Gly-Phe-Leu-Glu-Gly-Ala-Gly-Pro-Gly | (SEQ ID NO: 55) |
| Tyr-Gly-Gly-Phe-Met | (SEQ ID NO: 56) |
| Tyr-Gly-Gly-Phe-Leu | (SEQ ID NO: 57) |
| Tyr-D-Ala-Gly-Phe-Leu | (SEQ ID NO: 58) |
| Tyr-Gly-Gly-Phe | (SEQ ID NO: 59) |
| Tyr-D-Ala-Gly-Phe | (SEQ ID NO: 60) |

The composition of the present invention comprises a safe and effective amount of the peptide of the general formula (I), preferably at a level of from about 0.00001 to 10%, preferably 0.0001 to 0.1% by the weight of the entire composition.

As used herein, the term "cosmetic or cosmeceutical composition" refers to a composition that is applied topically to the human skin to improve the appearance and health of the skin. In this respect, the term "skin" encompasses whole skin or any portion of the skin, including hair, nails, etc.

As used herein, the term "dermatological composition" refers to a pharmaceutical composition formulated for cutaneous administration, such as formulated for the application to a portion of skin affected by a skin condition or a skin disorder. Nonexclusive examples of such disorders and conditions include reduced skin elasticity, decreased skin firmness, loss-of skin moisture, dry skin, pruritus, blotches, wrinkles, lentigines, age spots, melasmas, hyperpigmented skin, hyperkeratotic skin, skin atrophy, senile purpura, psoriasis, eczema, inflammatory dermatoses, spider veins, keratoses, and brittle hair or nails. Additional dermatologic conditions which can be treated with compositions of the present invention include those described in Freedberg et al., Fitzpatrick's Dermatology in General Medicine (6th Edition, 2003), Kerdel, et al., Dermatologic Therapeutics (2005), and Hardman et al., Goodman & Gilman's: The Pharmacological Basis of Therapeutics (10th Edition, 2001)

As used herein, the term "cosmetically acceptable carrier" refers to one or more liquid, semi-solid, or solid diluents, which are compatible with interleukin-1 alpha, and are suitable for administration to any portion of the human skin, hair, and nail suitable without undue/unacceptable aesthetic effects, e.g., greasiness, color, odor, etc. Examples of such carriers include, but are not limited to, distilled or deionized water, propyleneglycol, glycerol, and oil.

As used herein, the term "dermatologically acceptable carrier" refers to one or more liquid, semi-solid, or solid diluents, which are suitable for administration to any portion of the human skin, and are compatible with the interleukin-1 alpha and other active or optional ingredients of the present invention. Examples of such carriers include, but are not limited to, distilled or deionized water, propyleneglycol, glycerol, and oil.

The compositions of the present invention are useful for regulating the skin condition, visible and/or tactile discontinuities in skin (especially the skin surface; such discontinuities are generally undesirable). Such discontinuities may be induced or caused by internal and/or external factors, and include the signs of skin aging described herein. The term "regulating skin condition" includes prophylactically regulating and/or therapeutically regulating skin condition, including visible and/or tactile discontinuities in skin. As used herein, prophylactically regulating skin condition includes delaying, minimizing and/or preventing visible and/or tactile discontinuities in skin. As used herein, therapeutically regulating skin condition includes ameliorating, e.g., diminishing, minimizing and/or effacing, discontinuities in skin. Regulating skin condition involves improving skin appearance and/or feel. Also, the compositions of the present invention are particularly advantageous for treatment of acne and other skin disorders.

The compositions of the present invention are particularly advantageous for regulating signs of skin aging, more especially visible and/or tactile discontinuities in skin texture associated with aging. "Regulating the signs of skin aging" includes prophylactically regulating and/or therapeutically regulating one or more of such signs (similarly, regulating a given sign of skin aging, e.g., lines, wrinkles or pores, includes prophylactically regulating and/or therapeutically regulating that sign). As used herein, prophylactically regulating such signs includes delaying, minimizing and/or preventing signs of skin aging. As used herein, therapeutically regulating such signs includes ameliorating, e.g., diminishing, minimizing and/or effacing signs of skin aging.

"Signs of skin aging" include, but are not limited to, all outward visibly and tactilely perceptible manifestations as well as any other macro or micro effects due to skin aging.

Such signs may be induced or caused by intrinsic factors or extrinsic factors, e.g., chronological aging and/or environmental damage. These signs may result from processes which include, but are not limited to, the development of textural discontinuities such as wrinkles, including both fine superficial wrinkles and coarse deep wrinkles, skin lines, crevices, bumps, large pores (e.g., associated with adnexal structures such as sweat gland ducts, sebaceous glands, or hair follicles), scaliness, flakiness and/or other forms of skin unevenness or roughness, loss of skin elasticity (loss and/or inactivation of functional skin elastin), sagging (including puffiness in the eye area and jowls), loss of skin firmness, loss of skin tightness, loss of skin recoil from deformation, discoloration (including undereye circles), blotching, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues, especially those proximate to the skin.

The compositions of the present invention can comprise optional ingredients. Such optional ingredients generally are used individually at levels from about 0.0005% to about 10.0%, preferably from about 0.005% to about 1.0% by weight of the composition.

Examples of suitable optional ingredients include, but are not limited to, depigmentation agents; humectants; antimicrobial (e.g., antibacterial) agents; anti-acne agents; anti-aging agents; anti-wrinkling agents, antiseptics; local anesthetics; wound healing promoters; deodorants and antiperspirants; skin emollients and skin moisturizers; tanning agents; skin lightening agents; antifungals; depilating agents; external analgesics; counterirritants; anti-diaper rash agents; make-up preparations; vitamins and nutrients such as thiamin, riboflavin, niacin, pantothenates, pyridoxine, folic acid, cobalamin, biotin, choline, inositol, ascorbic acid, lipoic acid, carnitine, and etc.; amino acids and their derivatives such as alanine, arginine, asparagine, aspartic acid, carnitine, citrulline, cysteine, dimethylglycine, gamma-aminobutyric acid, glutamic acid, glutamine, glutathione, glycine, histidine, isoleucine, leucine, lysine, methionine, ornithine, phenylalanine, praline, serine, taurine, threonine, tryptophan, tyrosine, valine; minerals such as boron, calcium, chromium, cobalt, copper, fluoride, germanium, iodine, iron, lithium, magnesium, manganese, molybdenum, phosphorus, potassium, selenium, silicon, sodium, sulfur, vanadium, zinc; herbal extracts; retinoids; bioflavonoids; anti-oxidants; skin conditioners; hair lighteners; chelating agents; cell turnover enhancers; coloring agents; and mixtures thereof.

Examples of suitable humectants include, but not limited to, water soluble liquid polyols selected from the group comprising glycerine, propylene glycol, hexylene glycol, butylene glycol, pentylene glycol, dipropylene glycol, and mixtures thereof. The humectant is preferably present in an amount of from about 0 percent to about percent, more preferably from about 0.5 percent to about 5 percent, based on the overall weight of the composition.

Suitable amino acid agents include amino acids derived from the hydrolysis of various proteins as well as the salts, esters, and acyl derivatives thereof. Examples of such amino acid agents nonexclusively include amphoteric amino acids such as alkylamido alkylamines, i.e. stearyl acetyl glutamate, capryloyl silk amino acid, caprylol collagen amino acids; capryloyl kertain amino acids; capryloyl pea amino acids; cocodimonium hydroxypropyl silk amino acids; corn gluten amino acids; cysteine; glutamic acid; glycine; hair keratin amino acids; hair amino acids such as aspartic acid, threonine, serine, glutamic acid, glycine, alanine, half-cystine, valine, methionine, isoleucine, leucine, tyrosine, phenylalanine, cysteic acid, lysine, histidine, arginine, cysteine, tryptophan, citrulline; lysine; silk amino acids, wheat amino acids; and mixtures thereof.

Examples of suitable proteins include, but not limited to, collagen, deoxyribonuclease, iodized corn protein; keratin; milk protein; protease; serum protein; silk; sweet almond protein; wheat germ protein; wheat protein; wheat protein, alpha and beta helix of keratin proteins; hair proteins, such as intermediate filament proteins, high-sulfur proteins, ultra-high-sulfur proteins, intermediate filament-associated proteins, high-tyrosine proteins, high-glycine tyrosine proteins, tricohyalin, arginine-rich peptides like as oligoarginines $(Arg)_8$, and mixtures thereof.

Examples of suitable antiperspirants and deodorants include, but not limited to, aluminium chlorohydrates, aluminium zirconium chlorohydrates, and mixtures thereof.

Examples of suitable counterirritants include, but not limited to, camphor, menthol, methyl salicylate, peppermint and clove oils, ichtammol, and mixtures thereof.

Examples of suitable anti-aging agents include, but are not limited to, inorganic sunscreens such as zinc oxide; organic sunscreens such as octyl-methyl cinnamates and derivatives thereof; retinoids; vitamins such as vitamin C, vitamin B, and derivatives thereof; antioxidants including acid such as glycolic acid, citric acid, lactic acid, malic acid, mandelic acid, ascorbic acid, alpha-hydroxybutyric acid, alpha-hydroxyisobutyric acid, alpha-hydroxyisocaproic acid, atrrolactic acid, alpha-hydroxyisovaleric acid, ethyl pyruvate, galacturonic acid, glucopehtonic acid, glucopheptono 1,4-lactone, gluconic acid, gluconolactone, glucuronic acid, glucurronolactone, glycolic acid, isopropyl pyruvate, methyl pyruvate, mucic acid, pyruvia acid, saccharic acid, saccaric acid 1,4-lactone, tartaric acid, and tartronic acid; succinic acid or salts thereof; acids such as beta-hydroxybutyric acid, beta-phenyllactic acid, beta-phenylpyruvic acid; botanical extracts such as green tea, soy, milk thistle, algae, aloe, angelica, bitter orange, coffee, goldthread, grapefruit, hoellen, honeysuckle, Job's tears, lithospermum, mulberry, peony, puerarua, rice, safflower, and mixtures thereof. Suitable amounts of anti-aging agents include, based upon the total weight of the composition, from about 0.01 percent to about 10 percent, and preferably from about 0.04 percent to about 5 percent.

Examples of suitable depigmentation agents include, but are not limited to, hydroquinone and it derivatives; vitamins such as niacin, vitamin C and its derivatives; extracts such as chamomile and green tea, and mixtures thereof.

Examples of skin lightening agents include, but not limited to, hydroquinone, catechol and its derivatives, ascorbic acid and its derivatives, and mixtures thereof.

The compositions of the invention are prepared by well-known procedures. Such procedures include, but are not limited to, mixing the interleukin-1 alpha with other ingredients of the composition in conventional manner. Guidance for the preparation of cosmetic or dermatological compositions of the invention can be found in "Remington: The science and practice of pharmacy" 20th ed. Mack Publishing, Easton Pa., 2000 ISBN 0-912734-04-3 and "Encyclopaedia of Pharmaceutical Technology", edited by Swarbrick, J. & J. C. Boylan, Marcel Dekker, Inc., New York, 1988 ISBN 0-8247-2800-9 or a newer edition. As well known to the skilled person, illustrative additives to dermatological compositions include, but is not limited to: ointment bases, solvents, buffering agents, pH-adjusting agents, preservatives, humectants, chelating agents, antioxidants, stabilizers, emulsifying agents, suspending agents, gel-forming agents, perfumes, and skin protective agents.

The compositions of the present invention can be formulated in a variety of forms including, but are not limited to, lotions, gels, creams, sprays, and solutions. The compositions of the invention are prepared by methods well-known from the art in accordance with accepted procedures in a variety of forms. Such forms include, but are not limited to, solution, lotion, gel, emulsion, spray, and cream.

The compositions of the present invention are useful for regeneration of damaged hair and stimulating hair growth in subjects in need thereof. Also, the compositions of the present invention are particularly advantageous to improve nail health and appearance, accelerate nail growth and regeneration, to make nails more strength and flexible, and eliminate nail problems such as changes in the shape and texture of nails, thickened nails, nail fragility, and brittle nails.

The compositions of the present invention are particularly advantageous for regulating regional fat deposits including cellulite. The term "regional fat deposits" means areas of excessive fat, of which cellulite is an example, and excess fatty tissue. The term "cellulite" means deposits of fat, which generally do not respond to dieting and exercise. Cellulite is not the only cosmetic condition that concerns women. Stretch marks are another example of a cosmetic condition which affects not only women, but also men.

Further, the present invention provides a method for the cosmetic treatment comprising a step of applying an effective amount of the composition of the invention to the skin, hair or nail of a subject in need thereof. In the method of the invention, an effective amount of the composition of the invention is topically applied to the skin, and is preferably left on the skin for a period of at least about 15 minutes, more preferably at least about 30 minutes, even more preferably at least about 1 hour, most preferably for at least several hours, e.g., up to about 12 hours. This method can be reapplied from 1 to about 5, preferably from 1 to 3 times per day. Typically, the effective amount of the composition is from about 1 gram to about 100 grams, preferably from about 1 gram to about 20 grams.

Further, the present invention provides a method for the dermatologic treatment comprising a step of applying an effective amount of the composition of the invention to the skin of a subject in need thereof. In the method of the invention, an effective amount of the composition of the invention is topically applied to the skin, and is preferably left on the skin for a period of at least about 15 minutes, more preferably at least about 30 minutes, even more preferably at least about 1 hour, most preferably for at least several hours, e.g., up to about 12 hours. This method can be reapplied from 1 to about 5, preferably from 1 to 3 times per day. Typically, the effective amount of the composition is from about 1 gram to about 100 grams, preferably from about 1 gram to about 20 grams.

The following examples are presented to demonstrate the invention. The examples are illustrative only and are not intended to limit the scope of the invention in any way.

Example 1

This example demonstrates the pharmaceutical composition for injections.

| Ingredient | Content, wt. % |
|---|---|
| Interleukin 1 alpha | 0.000001 |
| Peptide of SEQ ID NO: 3 | 0.001 |
| Phosphate buffer | qs to pH 5.5 |
| WFI water | to 100 |

The solution preparation: ingredients are mixed in the conventional manner to prepare the composition.

Example 2

This example demonstrates the cosmetic or cosmeceutical composition for skin care.

| Ingredient | Content, wt. % |
|---|---|
| Interleukin 1 alpha | 0.000001 |
| Peptide of SEQ ID NO: 3 | 0.001 |
| Ethylcellulose | 0.6 |
| Phosphate buffer | qs to pH 5.5 |
| Deionized water | to 100 |

The solution preparation: the liophylized solid composition is dissolved in 1000 ml of deionized water to prepare the solution and Ethylcellulose is added to form gel.

The method of the treatment of signs of aging skin with the use of the solution: 1 ml of the gel is topically applied to the facial skin, and is preferably left on the skin for a period of at least about 15 minutes.

Example 3

This example demonstrates the dermatological composition for the treatment of a sign of aging skin.

| Ingredient | Content, wt. % |
|---|---|
| Interleukin 1 alpha | 0.000001 |
| Peptide of SEQ ID NO: 27 | 0.0002 |
| Ethylcellulose | 0.3 |
| Phosphate buffer | qs to pH 5.5 |
| Deionized water | to 100 |

The gel preparation: ingredients are mixed in the conventional manner to prepare the gel dermatological composition.

The method for the treatment of wrinkles: 1 ml of the composition is topically applied to the facial skin in the area of wrinkles, and is preferably left on the skin for a period of at least about 15 minutes.

The invention claimed is:

1. A composition comprising:
   (a) interleukin-1 alpha; and
   (b) a peptide consisting of the amino acid sequence Tyr-D-Ala-Gly-Phe-Leu-Asp (SEQ ID NO: 3).

2. The composition of claim 1, wherein the content of interleukin-1 alpha in said composition is in the range from $10^{-7}$ to $10^{-4}$ wt. %.

3. The composition of claim 1, wherein the content of peptide in said composition is in the range from $10^{-4}$ to $10^{-1}$ wt. %.

4. The composition of claim 1, further comprising a buffer at a concentration effective to maintain the pH of the composition at between 4.0 to 7.5.

5. A pharmaceutical composition comprising:
   (a) interleukin-1 alpha;
   (b) a peptide consisting of the amino acid sequence Tyr-D-Ala-Gly-Phe-Leu-Asp (SEQ ID NO: 3); and
   (c) a pharmaceutically acceptable diluent or carrier.

6. The composition of claim 5, wherein the content of interleukin-1 alpha in said composition is in the range from $10^{-7}$ to $10^{-4}$ wt. %.

7. The composition of claim 5, wherein the content of the peptide in said composition is in the range from $10^{-4}$ to $10^{-1}$ wt. %.

8. The composition of claim 5, further comprising a buffer at a concentration effective to maintain the pH of the composition at between 4.0 to 7.5.

9. A dermatological composition comprising:
   (a) interleukin-1 alpha;
   (b) a peptide consisting of the amino acid sequence Tyr-D-Ala-Gly-Phe-Leu-Asp (SEQ ID NO: 3); and
   (c) a dermatologically acceptable diluent or carrier.

10. The composition of claim 9, wherein the content of interleukin-1 alpha in said composition is in the range from $10^{-7}$ to $10^{-4}$ wt. %.

11. The composition of claim 9, wherein the content of the peptide in said composition is in the range from $10^{-4}$ to $10^{-1}$ wt. %.

12. The composition of claim 9, further comprising a buffer at a concentration effective to maintain the pH of the composition at between 4.0 to 7.5.

13. A cosmetic composition comprising:
    (a) interleukin-1 alpha;
    (b) a peptide consisting of the amino acid sequence Tyr-D-Ala-Gly-Phe-Leu-Asp (SEQ ID NO: 3); and
    (c) a dermatologically acceptable diluent or carrier.

14. The composition of claim 13, wherein the content of interleukin-1 alpha in said composition is in the range from $10^{-7}$ to $10^{-4}$ wt. %.

15. The composition of claim 13, wherein the content of the peptide in said composition is in the range from $10^{-4}$ to $10^{-1}$ wt. %.

16. The composition of claim 13, further comprising a buffer at a concentration effective to maintain the pH of the composition at between 4.0 to 7.5.

* * * * *

SEQUENCE LISTING

<160> NUMBER OF SEQ ID NOS: 60

<210> SEQ ID NO 1
<211> LENGTH: 6
<212> TYPE: PRT

```
<213> ORGANISM: Artificial Sequence
<220> FEATURE:
<223> OTHER INFORMATION: Synthetic

<400> SEQUENCE: 1

Tyr Gly Gly Phe Leu Asp
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic

<400> SEQUENCE: 2

Tyr Ala Gly Phe Leu Asp
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic

<400> SEQUENCE: 3

Tyr Ala Gly Phe Leu Asp
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic

<400> SEQUENCE: 4

Tyr Gly Gly Phe Ile Asp
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic

<400> SEQUENCE: 5

Tyr Ala Gly Phe Ile Asp
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic

<400> SEQUENCE: 6

Tyr Ala Gly Phe Ile Asp
1               5

<210> SEQ ID NO 7
<211> LENGTH: 6
<212> TYPE: PRT
<213> ORGANISM: Artificial Sequence
<220> FEATURE:
```

```
<223> OTHER INFORMATION: Synthetic

<400> SEQUENCE: 7

Tyr Gly Gly Phe Met Asp
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic

<400> SEQUENCE: 8

Tyr Ala Gly Phe Met Asp
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic

<400> SEQUENCE: 9

Tyr Ala Gly Phe Met Asp
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic

<400> SEQUENCE: 10

Tyr Gly Gly Phe Val Asp
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic

<400> SEQUENCE: 11

Tyr Ala Gly Phe Val Asp
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

Tyr Ala Gly Phe Val Asp
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic
```

```
<400> SEQUENCE: 13

Tyr Gly Gly Phe Leu Asn
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic

<400> SEQUENCE: 14

Tyr Ala Gly Phe Leu Asn
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic

<400> SEQUENCE: 15

Tyr Ala Gly Phe Leu Asn
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic

<400> SEQUENCE: 16

Tyr Gly Gly Phe Ile Asn
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic

<400> SEQUENCE: 17

Tyr Ala Gly Phe Ile Asn
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic

<400> SEQUENCE: 18

Tyr Ala Gly Phe Ile Asn
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic

<400> SEQUENCE: 19
```

```
Tyr Gly Gly Phe Met Asn
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic

<400> SEQUENCE: 20

Tyr Ala Gly Phe Met Asn
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic

<400> SEQUENCE: 21

Tyr Ala Gly Phe Met Asn
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic

<400> SEQUENCE: 22

Tyr Gly Gly Phe Val Asn
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic

<400> SEQUENCE: 23

Tyr Ala Gly Phe Val Asn
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic

<400> SEQUENCE: 24

Tyr Ala Gly Phe Val Asn
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic

<400> SEQUENCE: 25

Tyr Gly Gly Phe Leu Glu
1               5
```

```
<210> SEQ ID NO 26
<211> LENGTH: 6
<212> TYPE: PRT
<213> ORGANISM: Artificial Sequence
<220> FEATURE:
<223> OTHER INFORMATION: Synthetic

<400> SEQUENCE: 26

Tyr Ala Gly Phe Leu Glu
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic

<400> SEQUENCE: 27

Tyr Ala Gly Phe Leu Glu
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28

Tyr Gly Gly Phe Ile Glu
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic

<400> SEQUENCE: 29

Tyr Ala Gly Phe Ile Glu
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic

<400> SEQUENCE: 30

Tyr Ala Gly Phe Ile Glu
1               5

<210> SEQ ID NO 31
<211> LENGTH: 6
<212> TYPE: PRT
<213> ORGANISM: Artificial Sequence
<220> FEATURE:
<223> OTHER INFORMATION: Synthetic

<400> SEQUENCE: 31

Tyr Gly Gly Phe Met Glu
1               5
```

```
<210> SEQ ID NO 32
<211> LENGTH: 6
<212> TYPE: PRT
<213> ORGANISM: Artificial Sequence
<220> FEATURE:
<223> OTHER INFORMATION: Synthetic

<400> SEQUENCE: 32

Tyr Ala Gly Phe Met Glu
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic

<400> SEQUENCE: 33

Tyr Ala Gly Phe Met Glu
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic

<400> SEQUENCE: 34

Tyr Gly Gly Phe Val Glu
1               5

<210> SEQ ID NO 35
<211> LENGTH: 6
<212> TYPE: PRT
<213> ORGANISM: Artificial Sequence
<220> FEATURE:
<223> OTHER INFORMATION: Synthetic

<400> SEQUENCE: 35

Tyr Ala Gly Phe Val Glu
1               5

<210> SEQ ID NO 36
<211> LENGTH: 6
<212> TYPE: PRT
<213> ORGANISM: Artificial Sequence
<220> FEATURE:
<223> OTHER INFORMATION: Synthetic

<400> SEQUENCE: 36

Tyr Ala Gly Phe Val Glu
1               5

<210> SEQ ID NO 37
<211> LENGTH: 6
<212> TYPE: PRT
<213> ORGANISM: Artificial Sequence
<220> FEATURE:
<223> OTHER INFORMATION: Synthetic

<400> SEQUENCE: 37

Tyr Gly Gly Phe Leu Gln
1               5

<210> SEQ ID NO 38
<211> LENGTH: 6
```

```
<212> TYPE: PRT
<213> ORGANISM: Artificial Sequence
<220> FEATURE:
<223> OTHER INFORMATION: Synthetic

<400> SEQUENCE: 38

Tyr Ala Gly Phe Leu Gln
1               5

<210> SEQ ID NO 39
<211> LENGTH: 6
<212> TYPE: PRT
<213> ORGANISM: Artificial Sequence
<220> FEATURE:
<223> OTHER INFORMATION: Synthetic

<400> SEQUENCE: 39

Tyr Ala Gly Phe Leu Gln
1               5

<210> SEQ ID NO 40
<211> LENGTH: 6
<212> TYPE: PRT
<213> ORGANISM: Artificial Sequence
<220> FEATURE:
<223> OTHER INFORMATION: Synthetic

<400> SEQUENCE: 40

Tyr Gly Gly Phe Ile Gln
1               5

<210> SEQ ID NO 41
<211> LENGTH: 6
<212> TYPE: PRT
<213> ORGANISM: Artificial Sequence
<220> FEATURE:
<223> OTHER INFORMATION: Synthetic

<400> SEQUENCE: 41

Tyr Ala Gly Phe Ile Gln
1               5

<210> SEQ ID NO 42
<211> LENGTH: 6
<212> TYPE: PRT
<213> ORGANISM: Artificial Sequence
<220> FEATURE:
<223> OTHER INFORMATION: Synthetic

<400> SEQUENCE: 42

Tyr Ala Gly Phe Ile Gln
1               5

<210> SEQ ID NO 43
<211> LENGTH: 6
<212> TYPE: PRT
<213> ORGANISM: Artificial Sequence
<220> FEATURE:
<223> OTHER INFORMATION: Synthetic

<400> SEQUENCE: 43

Tyr Gly Gly Phe Met Gln
1               5

<210> SEQ ID NO 44
<211> LENGTH: 6
<212> TYPE: PRT
<213> ORGANISM: Artificial Sequence
```

```
<220> FEATURE:
<223> OTHER INFORMATION: Synthetic

<400> SEQUENCE: 44

Tyr Ala Gly Phe Met Gln
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic

<400> SEQUENCE: 45

Tyr Ala Gly Phe Met Gln
1               5

<210> SEQ ID NO 46
<211> LENGTH: 6
<212> TYPE: PRT
<213> ORGANISM: Artificial Sequence
<220> FEATURE:
<223> OTHER INFORMATION: Synthetic

<400> SEQUENCE: 46

Tyr Gly Gly Phe Val Gln
1               5

<210> SEQ ID NO 47
<211> LENGTH: 6
<212> TYPE: PRT
<213> ORGANISM: Artificial Sequence
<220> FEATURE:
<223> OTHER INFORMATION: Synthetic

<400> SEQUENCE: 47

Tyr Ala Gly Phe Val Gln
1               5

<210> SEQ ID NO 48
<211> LENGTH: 6
<212> TYPE: PRT
<213> ORGANISM: Artificial Sequence
<220> FEATURE:
<223> OTHER INFORMATION: Synthetic

<400> SEQUENCE: 48

Tyr Ala Gly Phe Val Gln
1               5

<210> SEQ ID NO 49
<211> LENGTH: 6
<212> TYPE: PRT
<213> ORGANISM: Artificial Sequence
<220> FEATURE:
<223> OTHER INFORMATION: Synthetic

<400> SEQUENCE: 49

Tyr Ala Gly Phe Leu Arg
1               5

<210> SEQ ID NO 50
<211> LENGTH: 6
<212> TYPE: PRT
<213> ORGANISM: Artificial Sequence
<220> FEATURE:
<223> OTHER INFORMATION: Synthetic
```

```
<400> SEQUENCE: 50

Tyr Ala Gly Phe Leu Gly
1               5

<210> SEQ ID NO 51
<211> LENGTH: 6
<212> TYPE: PRT
<213> ORGANISM: Artificial Sequence
<220> FEATURE:
<223> OTHER INFORMATION: Synthetic

<400> SEQUENCE: 51

Tyr Ala Gly Phe Leu Lys
1               5

<210> SEQ ID NO 52
<211> LENGTH: 6
<212> TYPE: PRT
<213> ORGANISM: Artificial Sequence
<220> FEATURE:
<223> OTHER INFORMATION: Synthetic

<400> SEQUENCE: 52

Tyr Ala Gly Phe Leu Thr
1               5

<210> SEQ ID NO 53
<211> LENGTH: 6
<212> TYPE: PRT
<213> ORGANISM: Artificial Sequence
<220> FEATURE:
<223> OTHER INFORMATION: Synthetic

<400> SEQUENCE: 53

Tyr Ala Gly Phe Leu Ser
1               5

<210> SEQ ID NO 54
<211> LENGTH: 6
<212> TYPE: PRT
<213> ORGANISM: Artificial Sequence
<220> FEATURE:
<223> OTHER INFORMATION: Synthetic

<400> SEQUENCE: 54

Tyr Ala Gly Phe Leu Pro
1               5

<210> SEQ ID NO 55
<211> LENGTH: 11
<212> TYPE: PRT
<213> ORGANISM: Artificial Sequence
<220> FEATURE:
<223> OTHER INFORMATION: Synthetic

<400> SEQUENCE: 55

Tyr Ala Gly Phe Leu Glu Gly Ala Gly Pro Gly
1               5                   10

<210> SEQ ID NO 56
<211> LENGTH: 5
<212> TYPE: PRT
<213> ORGANISM: Artificial Sequence
<220> FEATURE:
<223> OTHER INFORMATION: Synthetic

<400> SEQUENCE: 56
```

```
Tyr Gly Gly Phe Met
1               5

<210> SEQ ID NO 57
<211> LENGTH: 5
<212> TYPE: PRT
<213> ORGANISM: Artificial Sequence
<220> FEATURE:
<223> OTHER INFORMATION: Synthetic

<400> SEQUENCE: 57

Tyr Gly Gly Phe Leu
1               5

<210> SEQ ID NO 58
<211> LENGTH: 5
<212> TYPE: PRT
<213> ORGANISM: Artificial Sequence
<220> FEATURE:
<223> OTHER INFORMATION: Synthetic

<400> SEQUENCE: 58

Tyr Ala Gly Phe Leu
1               5

<210> SEQ ID NO 59
<211> LENGTH: 4
<212> TYPE: PRT
<213> ORGANISM: Artificial Sequence
<220> FEATURE:
<223> OTHER INFORMATION: Synthetic

<400> SEQUENCE: 59

Tyr Gly Gly Phe
1

<210> SEQ ID NO 60
<211> LENGTH: 4
<212> TYPE: PRT
<213> ORGANISM: Artificial Sequence
<220> FEATURE:
<223> OTHER INFORMATION: Synthetic

<400> SEQUENCE: 60

Tyr Ala Gly Phe
1
```